(12) United States Patent
Whittaker (10) Patent No.: US 7,896,901 B2
(45) Date of Patent: Mar. 1, 2011

(54) TISSUE FIXATION DEVICE

(75) Inventor: Gregory R. Whittaker, Stoneham, MA (US)

(73) Assignee: DePuy Mitek, Inc., Raynham, MA (US)

( * ) Notice: Subject to any disclaimer, the term of this patent is extended or adjusted under 35 U.S.C. 154(b) by 589 days.

(21) Appl. No.: 11/860,006

(22) Filed: Sep. 24, 2007

(65) Prior Publication Data

US 2008/0051795 A1      Feb. 28, 2008

Related U.S. Application Data

(63) Continuation of application No. 10/445,682, filed on May 27, 2003, now Pat. No. 7,588,586.

(51) Int. Cl.
*A61B 17/08* (2006.01)

(52) U.S. Cl. ............... 606/232; 606/301; 606/304; 606/305

(58) Field of Classification Search ............ 606/232
See application file for complete search history.

(56) References Cited

U.S. PATENT DOCUMENTS

| | | | |
|---|---|---|---|
| 4,870,957 A | 10/1989 | Goble et al. | |
| 4,950,270 A | 8/1990 | Bowman | |
| 5,102,421 A * | 4/1992 | Anspach, Jr. | 606/232 |
| 5,151,104 A | 9/1992 | Kenna | |
| 5,152,790 A | 10/1992 | Rosenberg et al. | |
| 5,224,946 A | 7/1993 | Hayhurst et al. | |
| 5,268,001 A | 12/1993 | Nicholson et al. | |
| 5,324,308 A | 6/1994 | Pierce | |
| 5,405,359 A * | 4/1995 | Pierce | 606/232 |
| 5,443,482 A | 8/1995 | Stone et al. | |
| 5,480,403 A | 1/1996 | Lee | |
| 5,618,314 A | 4/1997 | Harwin et al. | |
| 5,632,748 A | 5/1997 | Beck, Jr. et al. | |
| 5,766,250 A | 6/1998 | Chervitz et al. | |
| 5,782,866 A * | 7/1998 | Wenstrom, Jr. | 606/232 |
| 5,868,789 A | 2/1999 | Huebner | |
| 5,871,504 A | 2/1999 | Eaton et al. | |
| 5,899,938 A | 5/1999 | Sklar et al. | |
| 5,931,840 A | 8/1999 | Goble et al. | |
| 5,948,001 A | 9/1999 | Larsen | |
| 5,961,520 A | 10/1999 | Beck, Jr. et al. | |
| 5,964,764 A | 10/1999 | West, Jr. et al. | |

(Continued)

FOREIGN PATENT DOCUMENTS

WO    WO-98/22048    5/1998

(Continued)

*Primary Examiner*—Corrine M McDermott
*Assistant Examiner*—Christopher D Prone (57) ABSTRACT

A tissue fixation device is provided that is preferably used to secure a ligament or graft within a prepared bone tunnel, for example in ACL replacement. The tissue fixation device generally includes an elongate member having a shaft portion that is adapted to be at least partially disposed within a bone tunnel, and a guide member that forms a portion of the proximal end of the elongate member. The guide member has a graft-seating surface that is effective to seat a graft and to position the graft toward one side of a bone tunnel when the device is disposed within the bone tunnel. The device also includes a graft-retaining member formed on at least a portion of the graft-seating surface.

18 Claims, 5 Drawing Sheets

U.S. PATENT DOCUMENTS

| | | |
|---|---|---|
| 6,001,100 A | 12/1999 | Sherman et al. |
| 6,036,694 A | 3/2000 | Goble et al. |
| 6,214,007 B1 | 4/2001 | Anderson |
| 6,302,888 B1 | 10/2001 | Mellinger et al. |
| 6,322,563 B1 * | 11/2001 | Cummings et al. .......... 606/916 |
| 6,379,361 B1 | 4/2002 | Beck, Jr. et al. |
| 6,712,849 B2 | 3/2004 | Re |
| 7,588,586 B2 | 9/2009 | Whittaker |
| 2001/0021858 A1 | 9/2001 | Bolduc et al. |

FOREIGN PATENT DOCUMENTS

| | | |
|---|---|---|
| WO | WO-02/32345 | 4/2002 |

* cited by examiner

TISSUE FIXATION DEVICE

CROSS-REFERENCE TO RELATED APPLICATIONS

The present invention is a continuation of U.S. application Ser. No. 10/445,682 filed on May 27, 2003 and entitled "Tissue Fixation Device, now U.S. Pat. No. 7,588,586." which is hereby incorporated by reference in its entirty.

FIELD OF THE INVENTION

The present invention relates to tissue fixation devices, and in particular to a ligament anchor device for use in arthroscopic surgical procedures.

BACKGROUND OF THE INVENTION

The complete or partial detachment of ligaments, tendons or other soft tissues from their associated bones within the body is a relatively common injury, particularly among athletes. Such injuries generally result from excessive stresses being placed on these soft tissues. For example, a tissue-detaching injury may occur as the result of an accident such as a fall, overexertion during a work-related activity, during the course of an athletic event, or in any one of many other situations and/or activities.

In the case of a partial detachment, commonly referred to under the general term "sprain," the injury will frequently heal itself, if given sufficient time, and if care is taken not to expose the injury to any undue or extraordinary stress during the healing process. If, however, the ligament or tendon is completely detached from its associated bone or bones, or if it is severed as the result of a traumatic injury, partial or permanent disability may result. Fortunately, a number of surgical techniques exist for re-attaching such detached tissues and/or completely replacing severely damaged tissues.

One such technique involves the re-attachment of the detached tissue using traditional attachment devices such as metal staples, sutures, and cancellous bone screws. Such "traditional" attachment devices have also been used to attach tendon or ligament substitutes (often formed of autogenous tissue harvested from elsewhere in the body) to the desired bone or bones. Another technique is described in detail in U.S. Pat. No. 4,950,270 entitled "Cannulated Self-Tapping Bone Screw" issued Aug. 21, 1990 to Bowman et al., which is incorporated herein by reference in its entirety. In this technique, an anterior cruciate ligament in a human knee, for example, is replaced and/or repaired by forming bone tunnels through the tibia and/or femur at the points of normal attachment of the anterior cruciate ligament. A ligament graft, with a bone plug on at least one of its ends, is sized to fit within the bone tunnels. Suture is then attached to the outer end of each bone plug, and thereafter passed through the femoral and/or tibial bone tunnels. The femoral plug and/or the tibial plug is/are then inserted into the appropriate bone tunnel behind the suture. Subsequently, the suture is drawn tight (simultaneously in opposite directions, in cases where bone plugs are to be located in both a femoral bone tunnel and a tibial bone tunnel). This procedure positions the bone plug (or plugs) in the desired location, and imparts the desired degree of tension to the ligament or ligament substitute. Finally, while holding the bone plugs in position, a bone screw is inserted between each bone plug and the side wall of its associated bone tunnel so as to securely lock the bone plug in position using a tight interference fit.

With the advancement of anterior cruciate ligament surgery from the open reconstructions to arthroscopic-endoscopic reconstructions, surgeons are faced with a number of choices concerning graft fixation, both at the femur and the tibia. These ligament fixation devices have been introduced to the orthopaedic community, often with mechanical studies that bear little relevance to the actual demands of postsurgical rehabilitation and return to sports mechanics. Thus, it can be difficult for the surgeon to determine those fixation devices that will prove the most reliable during early healing stages.

A number of principles have been established in the last decade concerning anterior cruciate ligament (ACL) surgery, which when adhered to usually result in an excellent outcome. Anatomic placement, no femoral condylar notch impingement, early range of motion, and strong, rigid fixation are but a few of these important principles. Some current devices, however, cannot withstand repeated cycling motions without loss of fixation strength. Moreover, depending on the fixation point of the graft within the bone tunnel, the graft can wear against the bone eventually resulting in tearing or breakage of the graft.

Accordingly, there is a need for an improved tissue fixation device that provides a strong, rigid fixation, and that avoids the risk of tearing or breakage of the graft.

SUMMARY OF THE INVENTION

The present invention generally provides a tissue fixation device having an elongate member adapted to be at least partially disposed within a bone tunnel and including proximal and distal ends with a longitudinal axis extending therebetween. A guide member, which is formed on a portion of the proximal end of the elongate member, includes a graft-seating surface effective to seat a graft and to position the graft toward one side of the bone tunnel when the tissue fixation device is disposed within the bone tunnel. The device further includes a graft-retaining member formed on at least a portion of the graft-seating surface.

In one embodiment, the graft-seating surface of the guide member can be substantially planar and an opposed, bone-contacting surface can be substantially convex. A proximal end of the guide member can optionally have a substantially hemispherical cross section. The guide member can also include a height and a width that increases in a distal-to-proximal direction. Preferably, at least a portion of the graft-seating surface extends along an inclined plane that intersects the longitudinal axis. In an exemplary embodiment, the inclined portion of the graft-seating surface extends at an angle in the range of about 5° to 45°.

In another embodiment, the graft-retaining member can be in the form of an eyelet adapted to receive and retain a graft. The opening in the eyelet preferably defines an axis extending therethrough that is substantially transverse to the longitudinal axis of the elongate member. The graft-retaining member can optionally extend between the proximal end of the elongate member and the graft-seating surface of the guide member. In particular, a first wall can be mated to the proximal end of the elongate member and can extend in a direction substantially parallel to the longitudinal axis, and a second wall can be mated to the graft-seating surface of the guide member and can extend in a direction substantially transverse to the first wall. In one embodiment, the graft-retaining member defines a substantially rectangular-shaped opening for receiving and retaining a graft.

In other aspects, the distal end of the elongate member can be adapted to be disposed within an expandable sleeve that is able to be disposed within a bone tunnel. The distal end of the elongate member can include sleeve-expanding ridges that assist in securing the elongate member within a bone tunnel. Each ridge is preferably in the shape of wedge-like member circumferentially formed about the distal end of the elongate member and having a diameter that increases distally to proximally.

In yet another embodiment, at least one suture-receiving structure can be formed on the guide member to receive suture to secure a graft to the guide member. The suture-receiving structure preferably comprises first and second bores extending through the guide member from the graft-seating surface to an opposed, bone-contacting surface in a direction substantially transverse to the axis of the elongate member. The suture-receiving structure can further include a trough formed in the bone-contacting surface and extending between the first and second bores.

In another embodiment, the present invention provides a tissue fixation device that is adapted to anchor soft tissue to bone. The device includes an elongate member having a distal shaft with a proximal, graft-retaining head disposed thereon. A longitudinal axis extends through the elongate member. A wedge-shaped guide member extends proximally from the graft-retaining head and includes an inclined graft-seating surface oriented in a plane that intersects the longitudinal axis of the elongate member. The graft-seating surface is effective to orient and maintain a graft in a desired position. The graft-seating surface can have a variety of configurations, but is preferably substantially planar and includes an opposed, bone-contacting surface having a hemispherical shape.

The present invention also provides methods for attaching a tissue graft to bone.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
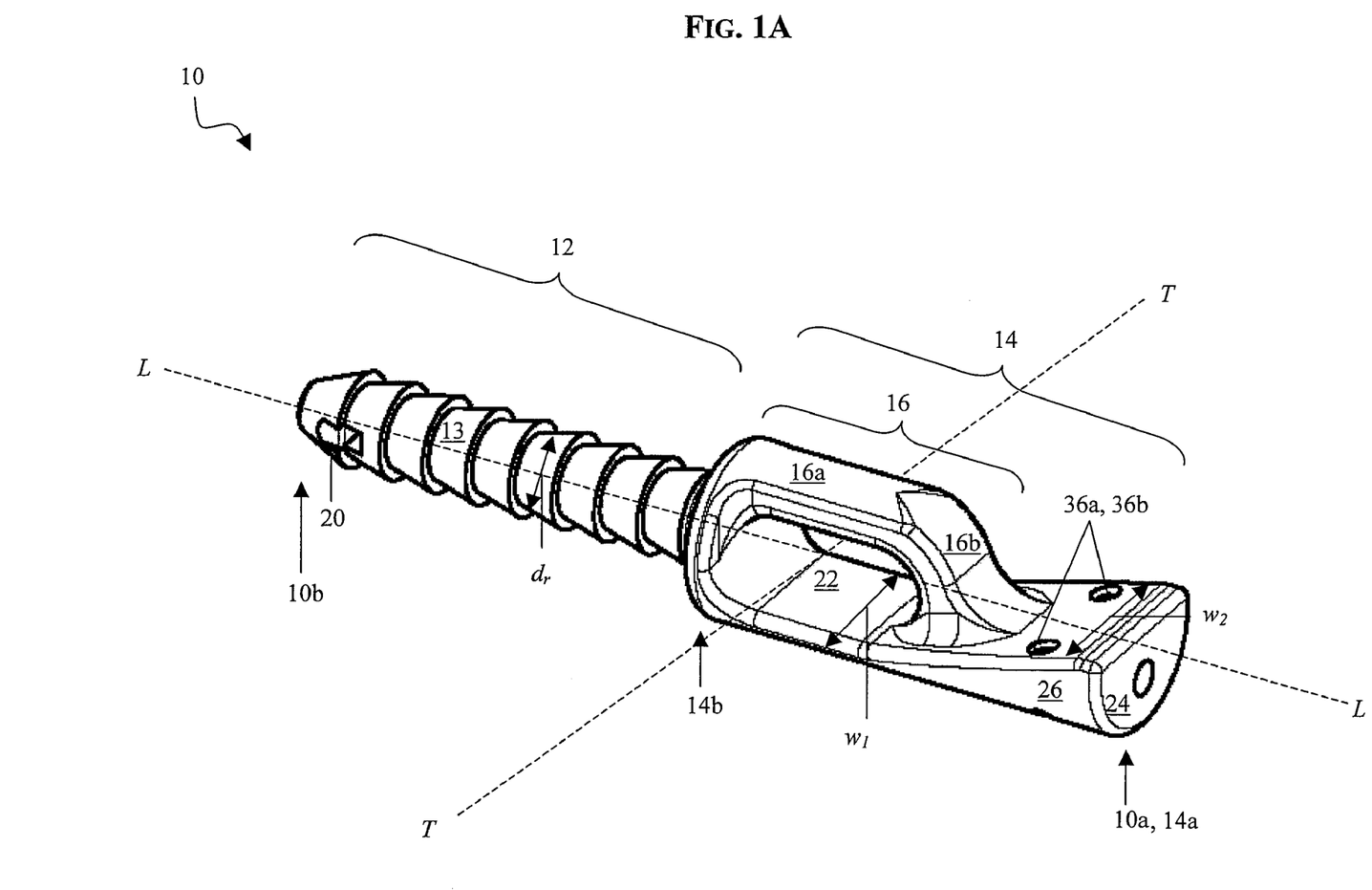
FIG. 1A is a perspective view of one embodiment of a tissue fixation device according to the present invention.

In general, the present invention provides a tissue fixation device that is preferably used to secure a ligament or graft within a prepared bone tunnel, for example in ACL replacement. As shown in FIG. 1A, the tissue fixation device 10 generally includes an elongate member having proximal and distal ends 10a, 10b. The distal portion is in the form of a shaft portion 12 that is adapted to be at least partially disposed within a bone tunnel, and a guide member 14 forms a portion of the proximal end of the elongate member. The guide member 14 has a graft-seating surface 22 effective to seat a graft and to position the graft toward one side of a bone tunnel when the device 10 is disposed within the bone tunnel. The device 10 also includes a graft-retaining member 16 formed on at least a portion of the graft-seating surface 22. The tissue fixation device 10 is particularly advantageous in that the graft guide 14 provides a strong, rigid fixation, and avoids compression of the graft by preventing the graft from wearing against the edge of the bone tunnel, which can eventually result in tearing or breakage of the graft. While the tissue fixation device 10 is described for use in ACL surgery, a person skilled in the art will appreciate that the device 10 can be used for a variety of medical purposes.

Figure 1B:
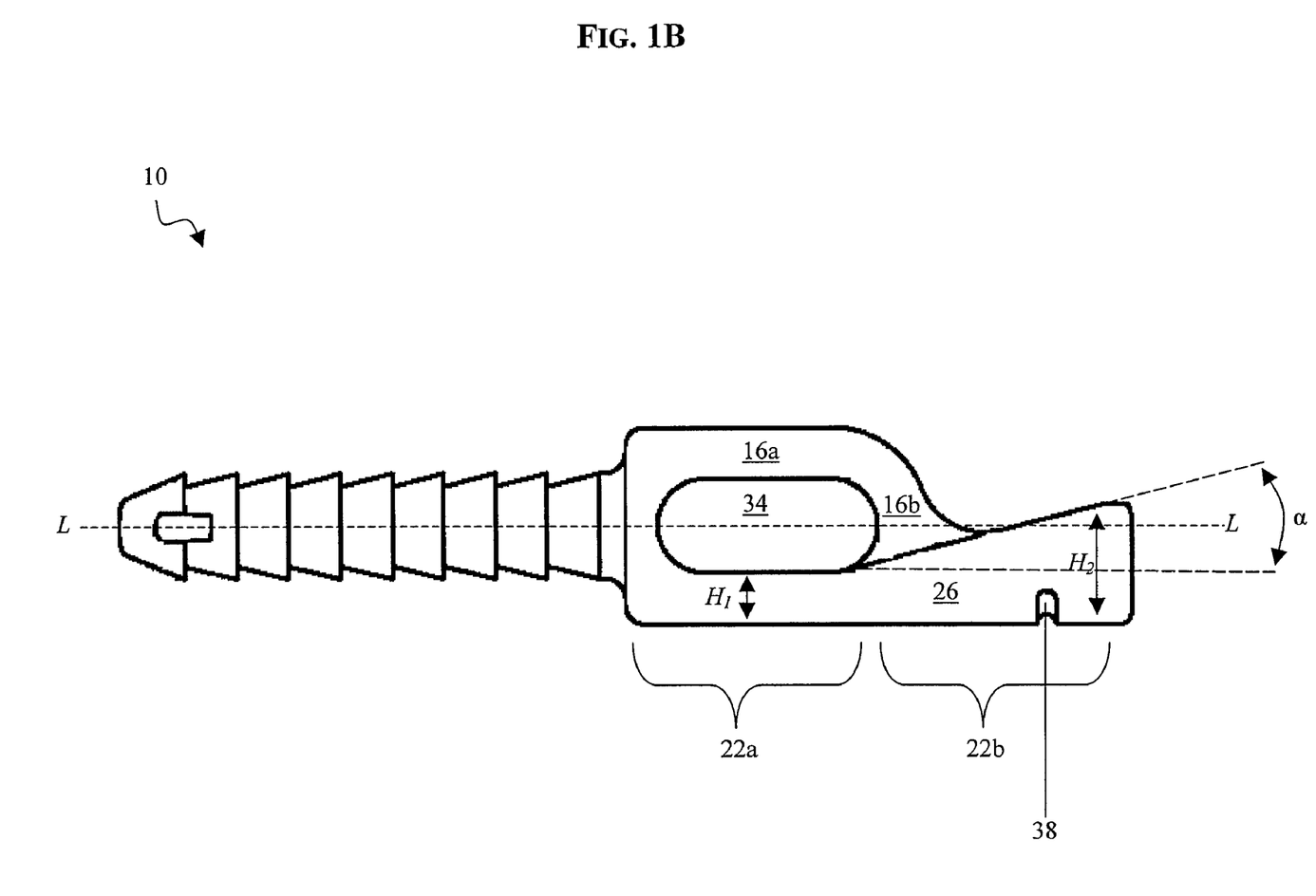
FIG. 1B is a side view of the tissue fixation device shown in FIG. 1A.

The shaft portion 12 of the device 10 can have a variety of configurations, and can be adapted to be embedded directly into a bone tunnel, or alternatively it can be adapted to be disposed within another implant (e.g., a sleeve) to facilitate the secure placement of the tissue fixation device within the bone tunnel. Preferably, the device 10 is used with a sleeve, such as the sleeve shown in FIG. 3 and described in U.S. No. 4,870,957 of Goble et al., which is incorporated herein by reference in its entirety. As shown in FIGS. 1A and 1B, the shaft 12 can include a series of sleeve-expanding ridges 13 that assist in securing the shaft 12 within a sleeve 18. Each ridge 13 can have a variety of shapes and sizes, but preferably each ridge 13 is in the shape of a wedge-like member circumferentially formed about the shaft 12, and having a diameter $d_r$ that increases in a distal-to-proximal direction. The shaft 12 can also optionally include a transverse bore 20, or similar structure, formed therein for receiving a suture which can be used to pull the device 10 through a bone tunnel and into the sleeve 18.

The guide member portion 14 of the device 10 is positioned proximal to the shaft 12, and forms the proximal head of the device 10. The guide member 14 can have a variety of configurations, shapes, and sizes, but it should be designed to be effective to seat a graft and to position the graft toward one side of a bone tunnel when the tissue fixation device 10 is disposed within the bone tunnel. In one embodiment, the guide member extends a distance beyond the graft-retaining member 16 in a proximal direction to form an extension member on the device 10. This extension of the device allows the device 10 to be inserted further into a bone tunnel, thereby providing a strong, rigid fixation, and provides an additional surface for the graft to rest on.

FIGS. 1A and 1B illustrate an exemplary embodiment of a guide member 14 having a generally elongate shape and including a substantially planar, graft-seating surface 22, an opposed, bone-contacting surface 26 that has a substantially convex shape, and a proximal end wall 24 having a hemispherical shape. The proximal portion 22b of the guide member 14 can have a flared or wedge-like shape to facilitate the placement of a graft disposed on the graft-seating surface 22 toward one side of a bone tunnel when the tissue fixation device 10 is disposed within the bone tunnel. This is further illustrated in FIG. 2, which shows the proximal end surface 24 of the guide member 14 having a substantially hemispherical shape, so as to occupy about one-half of the bone tunnel 30, thereby forcing the graft 32 to remain in the other half of the bone tunnel 30.

The wedge-like or flared shape of the proximal portion, shown in more detail in FIG. 1B, can be achieved by providing a graft-seating surface 22 having a distal portion 22a with a substantially constant height $H_1$ and a proximal portion 22b with a height $H_2$ that increases in a distal-to-proximal direction. The angle a of the proximal, graft-seating surface 22b, e.g., the inclined portion, can vary, but in an exemplary embodiment the proximal graft-seating surface 22b extends at an angle $\alpha$ in the range of about 5° to 45°. Referring back to FIG. 1A, the proximal graft-seating surface 22b also includes a width $W_2$ that can increase in a distal-to-proximal direction, and the distal graft-seating surface 22a can have a substantially constant width $W_1$.

A person skilled in the art will appreciate that the graft-seating surface 22 can vary in shape and size, and can have a substantially constant height and width, or a height and width that varies between the proximal and distal ends 14a, 14b of the guide member 14. Moreover, the device 10 is not limited to having a hemispherical sidewall, but rather can include any number of sidewalls having any sidewall shape. The device 10 can also optionally include other features, such as bone-engaging surface features, formed on the sidewall(s) to facilitate the secure placement of the device 10 within a bone tunnel.

In an exemplary embodiment, the guide member 14 can also include first and second bores 36a, 36b extending through the graft-seating surface 22 to the opposed, bone-contacting surface 26 in a direction substantially transverse to the longitudinal axis L of the device 10. The guide member 14 can also optionally include a trough 38, shown in FIG. 1B, formed in the bone-contacting surface 26 and extending between the first and second suture-receiving bores 36a, 36b. The trough 38 is effective to seat the suture sub-flush with the bone-contacting surface 26, thus preventing movement of the suture along the convex bone-contacting surface 26, and preventing the suture from coming into contact with the bone tunnel. In use, two free ends of a suture are passed through the bores 36a, 36b such that a portion of the suture extending between the free ends rests in the trough 38. The free ends of the suture can then be tied around a graft to secure the graft to the graft-seating surface 22 of the guide member 14. A person skilled in the art will appreciate that a variety of alternative techniques can be used to secure one or more grafts to the graft-seating surface 22 of guide member 14.

Figure 2:
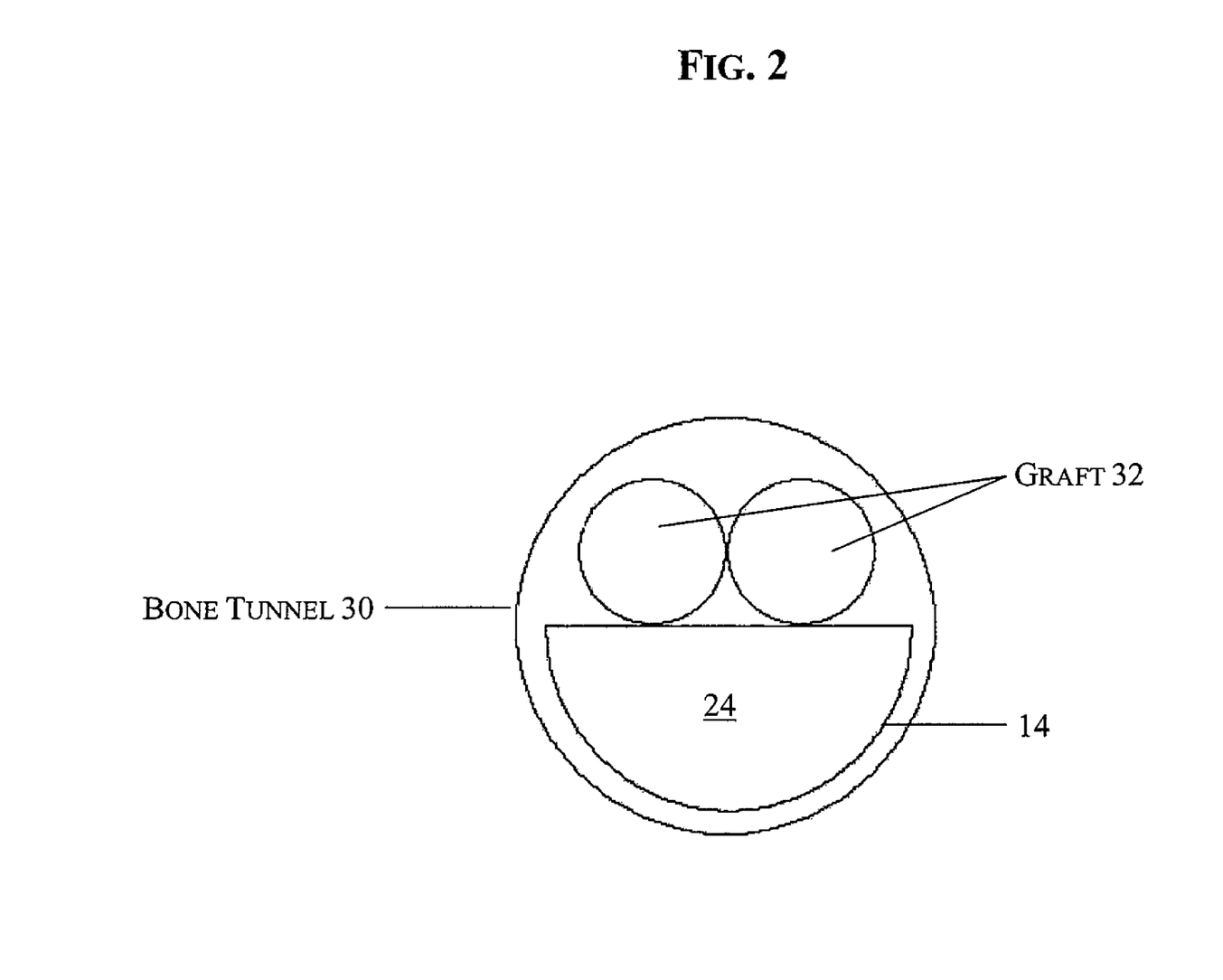
FIG. 2 is a proximal end view illustration of an opening of a bone tunnel having the tissue fixation device of FIG. 1A and a graft disposed therein.

Referring back to FIG. 1A, the device 10 further includes a graft-retaining member 16 formed on at least a portion of the graft-seating surface 22. In an exemplary embodiment, the graft-retaining member 16 is formed on the distal portion 22a of the guide member 12 to allow a graft to be looped through the graft-retaining member 16 and to rest on the graft-seating surface 22. The graft-retaining member 16 can have a variety of configurations, shapes, and sizes. As shown in FIG. 1A, the graft-retaining member 16 is generally in the form of an eyelet having an opening 34 adapted to receive a graft. The eyelet is formed from a first, longitudinal wall 16a that extends between a proximal end of the shaft 12 and that mates to a second, substantially transverse wall 16b that is joined to the graft-seating surface 22. The first and second walls 16a, 16b can be integrally formed with one another, as well as with the guide member 14 and/or the shaft 12 (i.e., as a result of a molding process). Moreover, the shape of each wall 16a, 16b, as well as the shape of the opening 34 defined by the walls 16a, 16b, can vary. In one embodiment, however, the walls 16a, 16b that form the graft-retaining member 16 are slightly rounded or curved to prevent damage to a graft disposed through the opening 34 formed by the walls 16a, 16b. The walls 16a, 16b also preferably form an opening 34 having a shape and size that facilitates placement of a graft therethrough. As shown in FIG. 1A, the opening 34 has a substantially rectangular shape. The position of the opening 34 can also vary, but preferably the opening 34 defines an axis T that extends in a direction substantially transverse to a longitudinal axis L of the device 10. This further facilitates placement of a graft through the opening 34, and placement of the two free ends of the graft onto the graft-seating surface 22 of the guide member 14, as shown in FIGS. 2 and 3.

A person skilled in the art will appreciate that a variety of graft-retaining members can be used with the device 10 of the present invention. By way of non-limiting example, the graft-retaining member can have a partially open, hook-like configuration, or any other configuration that allows a graft to be retained by the device 10.

Figure 3A:
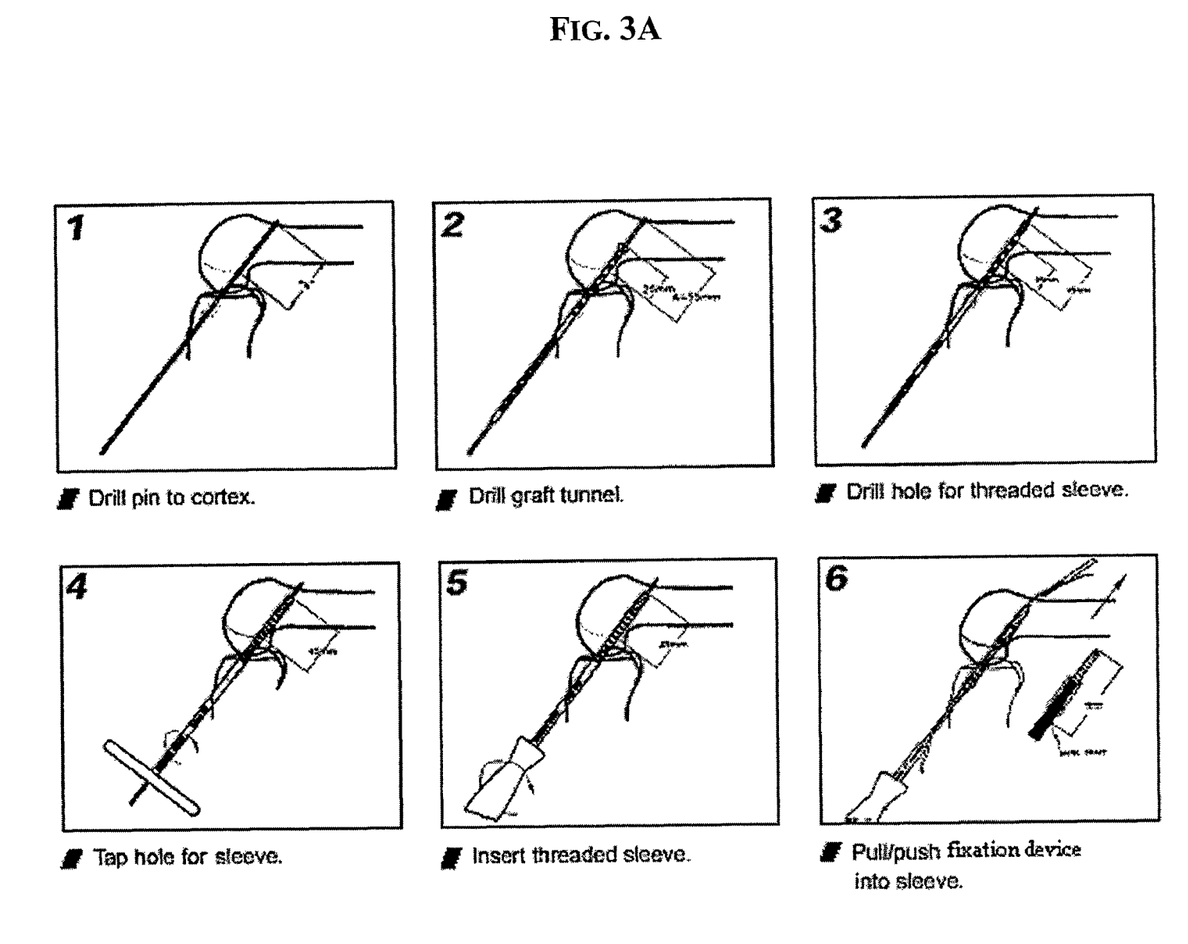
FIG. 3A is a chart illustrating an exemplary procedure for implanting a device according to the present invention.
Figure 3B:
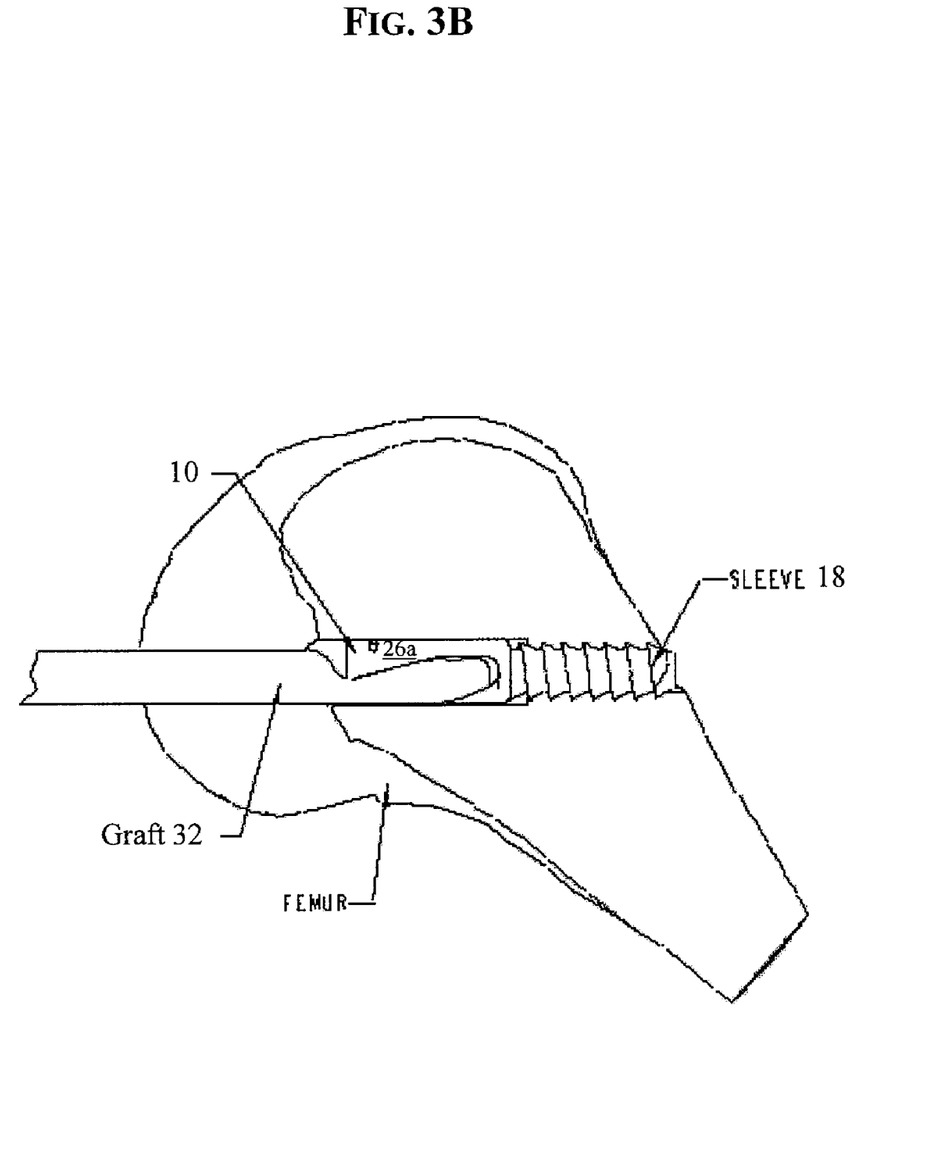
FIG. 3B is a side view illustration of the tissue fixation device of FIG. 1A disposed within an expandable sleeve in a bone tunnel formed in a patient's femur.

FIGS. 3A and 3B illustrate an exemplary embodiment for using the device 10 to repair an anterior cruciate ligament. Soft tissue grafts, such as the semitendinosus, can be attached to the graft-retaining member 16, preferably by quadrupling the graft through the graft-retaining member 16, or by combining tendons that are doubled through the graft-retaining member 16. A whip stitch can be used to facilitate pulling of the graft through the graft-retaining member 16. Once the graft is threaded through the graft-retaining member, the graft 32 is then pulled in a proximal direction to cause the graft 32 to rest on the graft-seating surface 22, as shown in FIG. 3B. The graft 32 can optionally be secured to the graft-seating surface 22 using one or more sutures that are passed through suture-receiving structures, such as first and second bores 36a, 36b described above with respect to FIG. 1A. Once the graft is attached to the device 10, the graft and the device 10 are passed through a sizer to determine the appropriate diameter of the femoral and tibial tunnels.

In drilling the tunnel, it is extremely important that the entrance of the tibial tunnel to the knee be located accurately in relationship to the femoral notch. The usual position is slightly medial, approximately 5 millimeters from the posterior cruciate ligament and in the posterior portion of the native ACL footprint. The tip of a tibial guide, such as the Innovasive ACL tibial Guide manufactured by Mitek of Westwood, Mass., is inserted through the interior medial portal and locked on the tibia. A pin is then drilled in a proximal direction, as shown in FIG. 3A(1) at approximately a 45° angle to the horizontal axis of the tibial plateau. After the pin emerges in the intercondylar notch, the guide is removed and pin placement is visually checked by taking the knee through a range of motion. Once an acceptable position has been confirmed, the pin is further driven across the intercondylar notch and into the back of the femoral notch to properly mark the angle that the ACL graft will traverse as it proceeds from the tibia to the femur. The tibial tunnel and femoral attachment site for the graft on the lateral condylar notch can then be reamed around the guide pin, as shown in FIG. 3A(2). Another drill tip can then be passed over the pin through the tibial tunnel to create a socket in the femoral condyle for receiving sleeve 18, as shown in FIG. 3A(3). A pilot hole can then be tapped as shown in FIG. 3A(4), and sleeve 18 can be screwed into position as shown in FIG. 3A(5).

With the sleeve in place, an arthroscope can be inserted through the tibial tunnel, and the knee can be taken through a range of motion. If the intercondylar notch is seen impinging or overlapping the tibial tunnel, further notch plasty can be completed at this time. Once the notch-graft fit has been confirmed using the arthroscope, the pin is pushed retrograde, emerged distally through the tibial tunnel. The tissue fixation device 10 can now be pulled into the joint using the suture attached to the transverse bore 20 in the shaft 12, and attached to the pin. The pin exits the superior thigh, pulling the suture and the device 10 through the tibial tunnel into the sleeve 18, as shown in FIG. 3A(6). As the device 10 is pulled into the sleeve 18, the ridges 13 expand the sleeve 18 to engage the sleeve 18 to create an interference within the bone tunnel to prevent removal of the sleeve 18 and the fixation device 10 from the bone tunnel. Alternatively, or in addition, a pronged inserter (not shown) or similar tool may be used to push the device 10 into the sleeve 18.

The tissue fixation device 10 is preferably positioned within the bone tunnel such that the proximal end wall 24 of the guide member 14 is either aligned with the opening of the bone tunnel, or is disposed just within the opening of the bone tunnel, as shown in FIG. 3B. Moreover, the guide member 14 should be aligned within the tunnel (as shown in FIG. 3B) such that bending of the patient's knee will cause the graft 32 to the tension over the proximal end 14a of the guide member 14, rather than to tension against the edge of the opening of the bone tunnel which can potentially damage the graft 32. To complete the procedure, the remaining end of the graft is tension to and affixed to the anterior tibia using, for example, a screw and washer.

The device 10 can be formed from a variety of materials, and can be formed from separate parts which are mated to one another. Preferably, however, the device 10 is formed as a single unit from a material that is suitable for human implantation, such as metal or plastic, and that is somewhat resilient. Exemplary materials include, for example, metal, absorbable polymers, such as, but not limited to, polylactic acid, polyglycolic acid, and copolymers thereof, non-absorbable polymers, such as, but not limited to, polyethylene, polypropylene, and acetal, and bioceramic materials, such as blends of polymers containing tricalcium phosphate and hydroxy appetite.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A tissue fixation device, comprising:
   an elongate member adapted to be at least partially disposed within a bone tunnel and having proximal and distal ends with a longitudinal axis extending therebetween;
   a guide member formed on the proximal end of the elongate member and having a graft-seating surface configured to seat a graft, at least a portion of the graft-seating surface being inclined to position a graft toward one side of a bone tunnel when the tissue fixation device is disposed within the bone tunnel;
   a graft-retaining member extending outward from the graft-seating surface and configured to allow a graft to be looped therethrough and to rest on the graft-seating surface; and
   wherein the graft-retaining member is distal to the portion of the graft-seating surface which is inclined to position the graft toward one side of the bone tunnel when the tissue fixation device is disposed within the bone tunnel.

2. The device of claim 1, wherein the graft-seating surface of the guide member is substantially planar and an opposed, bone-contacting surface is substantially convex.

3. The device of claim 1, wherein the guide member has a height and a width that increases in a distal-to-proximal direction.

4. The device of claim 1, wherein a proximal end of the guide member has a substantially semi-circular cross section.

5. The device of claim 1, wherein the inclined plane intersects the longitudinal axis.

6. The device of claim 1, wherein at least a portion of the elongate member includes a plurality of ridges that assist in securing the elongate member within a bone tunnel.

7. The device of claim 6, wherein the plurality of ridges extend circumferentially about the elongate member.

8. The device of claim 7, wherein the plurality of ridges have a diameter that increases distally to proximally.

9. The device of claim 1, further comprising at least one suture-receiving structure formed on the guide member and adapted to receive suture to secure a graft to the guide member.

10. The device of claim 9, wherein the suture-receiving structure comprises at least one bore extending through the guide member.

11. A tissue fixation device, comprising:
   an elongate member adapted to be at least partially disposed within a bone tunnel and having proximal and distal ends with a longitudinal axis extending therebetween;
   a guide member formed on the proximal end of the elongate member and having a graft-seating surface configured to seat a graft, at least a portion of the graft-seating surface being inclined to position a graft toward one side of a bone tunnel when the tissue fixation device is disposed within the bone tunnel;
   a graft-retaining member extending outward from the graft-seating surface and configured to allow a graft to be looped therethrough and to rest on the graft-seating surface; and
   wherein the graft-retaining member defines an eyelet.

12. The device of claim 11, wherein an opening in the eyelet that has an axis extending therethrough that is substantially transverse to the longitudinal axis of the elongate member.

13. A tissue fixation device, comprising:
   an elongate member adapted to be at least partially disposed within a bone tunnel and having proximal and distal ends with a longitudinal axis extending therebetween;
   a guide member formed on the proximal end of the elongate member and having a graft-seating surface configured to seat a graft, at least a portion of the graft-seating surface being inclined to position a graft toward one side of a bone tunnel when the tissue fixation device is disposed within the bone tunnel; and
   a graft-retaining member extending outward from the graft-seating surface and configured to allow a graft to be looped therethrough and to rest on the graft-seating surface;
   wherein the graft-retaining member extends between the proximal end of the elongate member and the graft-seating surface of the guide member; and
   wherein the graft-retaining member includes a first wall mated to the proximal end of the elongate member and extending in a direction substantially parallel to the longitudinal axis, and second wall mated to the graft-seating surface of the guide member and extending in a direction substantially transverse to the first wall.

14. A tissue fixation device adapted to anchor soft tissue to bone, comprising:
   an elongate member having a distal shaft with a proximal graft-retaining head disposed thereon; and
   a wedge-shaped guide member extending proximally from the graft-retaining head and including a substantially planar inclined graft-seating surface and an opposed substantially convex bone-contacting surface, the graft-seating surface being configured to position a graft toward one side of a bone tunnel and the bone-contacting surface being configured to abut the opposed side of the bone tunnel.

15. The device of claim 14, wherein the guide member includes a proximal end having a substantially semi-circular cross section.

16. The device of claim 14, wherein the distal shaft of the elongate member includes a plurality of ridges that assist in securing the elongate member within a bone tunnel.

17. The device of claim 14, further comprising at least one suture-receiving structure formed on the guide member and adapted to receive suture to secure a graft to the guide member.

18. The device of claim 17, wherein the suture-receiving structure comprises at least one bore extending through the guide member.

* * * * *